(12) United States Patent
Remesy et al.

(10) Patent No.: US 6,616,939 B1
(45) Date of Patent: Sep. 9, 2003

(54) ENERGETIC REHYDRATION FLUID COMPOSITION IN PARTICULAR FOR YOUNG ANIMALS NO LONGER ABLE TO DIGEST MILK NORMALLY

(75) Inventors: Christian Remesy, Clermont-Ferrand (FR); Christian Demigne, Ceyrat (FR)

(73) Assignee: Institut National de la Recherche Agronomique (INRA), Paris (FR)

( * ) Notice: Subject to any disclaimer, the term of this patent is extended or adjusted under 35 U.S.C. 154(b) by 0 days.

(21) Appl. No.: 09/831,029

(22) PCT Filed: Nov. 3, 1999

(86) PCT No.: PCT/FR99/02676

§ 371 (c)(1),
(2), (4) Date: May 4, 2001

(87) PCT Pub. No.: WO00/25601

PCT Pub. Date: May 11, 2000

(30) Foreign Application Priority Data

Nov. 4, 1998 (FR) .............................................. 98 13847

(51) Int. Cl.$^7$ ........................... A23K 1/165; A23K 1/17

(52) U.S. Cl. ...................... 424/442; 424/400; 424/438; 424/439; 424/78.01; 426/2; 426/74; 426/629; 426/630; 426/635; 426/615; 426/807

(58) Field of Search ................................ 424/400, 438, 424/439, 442, 78.01; 426/74, 2, 629, 630, 635, 615, 807

(56) References Cited

U.S. PATENT DOCUMENTS

| | | | | |
|---|---|---|---|---|
| 4,309,417 A | * | 1/1982 | Staples ........................ | 424/601 |
| 4,652,454 A | * | 3/1987 | Remesy et al. ............. | 426/583 |
| 5,128,167 A | * | 7/1992 | De Laporte .................... | 426/2 |

* cited by examiner

Primary Examiner—Thurman K. Page
Assistant Examiner—Charesse Evans
(74) Attorney, Agent, or Firm—Foley & Lardner

(57) ABSTRACT

The invention concerns a rehydration fluid composition, useful in particular for feeding young animals no longer able to digest milk, comprising lactose or glucose or a product based on lactose or glucose: a mineral supplement ensuring restoration of digestive losses. The invention is characterised in that the composition further comprises an efficient quantity of soluble vegetable proteins and vegetable lipids ensuring suitable appropriate energy intake.

20 Claims, No Drawings

ENERGETIC REHYDRATION FLUID COMPOSITION IN PARTICULAR FOR YOUNG ANIMALS NO LONGER ABLE TO DIGEST MILK NORMALLY

The present invention relates to an energy-supplying rehydrating composition which can be used in particular for young animals, especially young ruminants, no longer able to digest milk normally.

Diarrhea in calves constitutes the main cause of morbidity during the first weeks of life, thus causing considerable economic losses for this cattle farm. Whatever its origin (nutritional, bacterial or viral), diarrhea is most commonly revealed by symptoms of severe dehydration of the animal and of digestive and metabolic modifications, these phenomena doubtless being linked. In conditions of diarrhea or in situations of stress likely to profoundly disturb the course of digestion, it is well known that it is necessary to partially or totally eliminate milk-based food. Specifically, the digestion of milk can be affected by disturbances in the emptying of the rennet stomach and, in this case, the administration of milk tends to worsen the physiological state since this may lead to total blocking of the functioning of the rennet stomach, which compromises the subsequent taking of any oral treatment.

Even though the processes of coagulum formation in the rennet stomach are not entirely destroyed, the possibilities for digesting proteins and lipids in the small intestine are decreased given the poor condition of the intestinal mucous membrane or insufficient pancreatic secretion. Even if the calf suffering from digestive problems manages to partially digest the milk-based food, this does not allow it to have an optimum amount of water and of minerals to deal with the exacerbated intestinal losses of water and of electrolytes. The mineral composition of milk appears to be intended for ensuring rapid growth of the various tissues, in particular of the bone tissues. For this reason, milk is rich in the phosphorus and calcium which are required for constructing bone, and in potassium, the major cation of the intracellular medium. The relative lack, in milk, of sodium and of chloride, which are lost in very high amounts during diarrhea, makes this food unsuitable for compensating the very high digestive losses of these minerals.

In addition, a sick animal appears to be quite incapable of assimilating energetic substrates for anabolism (synthesis of proteins and of lipids) subsequent to the metabolic disturbances caused by dehydration. The calf is, in fact, in reasonably serious acidosis subsequent to the accumulation of lactic acid and to the digestive loss of bicarbonate. Hypovolemia decreases the oxygenation of the tissues and, therefore, the metabolic capacity of the organs. The secretion of glucocorticoids causes intense nitrogen-based catabolism, which means that it is not possible to ensure normal tissue growth during this period. This set of factors means that the animals suffering from diarrhea show a reasonably high intolerance to milk. In fact, these animals need to receive minerals and water in order to restore the body's losses of electrolytes and blood volume.

The use of glucose, of disaccharides and of amino acids, coupled to a suitable supply of electrolytes, has been a basis for the preparation of many synthetic rehydrating substances.

An example of such a preparation is described in French patent No. 2 467 599, which relates to a rehydrating composition comprising, besides glucose, at least one amino acid which is free or in the form of a salt, in particular sodium glutamate and a sodium salt of $C_2$ to $C_8$ aliphatic carboxylic acid. It has, in fact, been shown that, at the digestive level, carbohydrates and/or amino acids are essential for promoting the active absorption of sodium and, therefore, that of water since the latter follows the solutes. Other glucose-based compositions have also been proposed.

However, these formulations, which are theoretically effective in correcting the problems of dehydration and mineral losses, do not enable the calves to combat the disease over a long period of time if they do not recover very rapidly. Specifically, in the form of simple carbohydrates or of free amino acids, the available energy supply is much too low. For reasons of osmotic pressure, it is difficult to supply a lot of energy in this form; in addition, an energy supply restricted to these two types of substrate does not satisfy all of the calf's needs.

A first attempt at resolving the nutritional problems of diarrheic calves has been described in patent FR 2 539 006, using lactose or lactoserum as a rehydration base. However, it is highly inadvisable to use products of animal origin, from diverse sources, in animals whose immune defenses are insufficient; specifically, the lactoserum-based products might contain various pathogenic agents which can be transmitted more easily when the digestive barrier is modified.

The problem which the present invention proposes to resolve consists in allowing animals no longer able to digest milk normally, in particular diarrheic calves, to have an energy supply suitable for their physiological condition; in particular, a supply of energy at the digestive level in order to promote the active absorption of sodium and, therefore, of water, and a supply of energy at the metabolic level since a minimum supply of energetic substrates, in the form of carbohydrates, of proteins and of lipids, is essential in order to optimize cellular functioning, to help cells conserve minerals and to help the body combat infection.

In addition, another problem resolved by the present invention is nevertheless avoiding an energy supply in the form of a dairy food, in any case in significant amount.

Another problem resolved by the present invention is avoiding the risk of transmitting pathogenic agents which are unconventional and resistant to the current treatment of dairy products (of prion type).

An object of the present invention is to propose a food composition which provides an energy supply of carbohydrates identical to that of milk.

The supply of carbohydrates, in the form of glucose or preferably in the form of the natural sugar present in milk, lactose, should be as abundant as possible. Once hydrolyzed, lactose is also involved in sodium cotransport, whether for the entry of glucose or of galactose into the enterocyte. The presence of lactose leads to the absorption of glucose and of galactose, which are the two sugars most suitable for the calf's physiology, even when it is sick.

Another object of the present invention is to propose a food composition which provides a supply of proteins representing 25 to 40% of the mean protein content of milk, but consisting entirely of proteins which are soluble and not precipitated in the rennet stomach.

The supply of proteins is, in particular, essential for providing glutamine, an essential energetic substrate of enterocytes, and also the other amino acids required for the accelerated renewal of the intestinal cells. During their degradation, amino acids or peptides can help the transport of sodium toward the enterocyte. A supply of very digestible proteins facilitates both intestinal regeneration, maintenance of the body pool of proteins and functioning of the cells of the immune system via certain specific amino acids (arginine, glutamine, etc.).

Another object of the present invention is to propose a food composition which provides a supply of lipids representing 25 to 40% of the mean lipid content of milk, but comprising mainly triglycerides of medium-chain fatty acids.

The supply of fatty acids, in particular of medium-chain fatty acids, is very important for thermogenesis, for stimulating the use of lactate in the liver and for glucose sparing.

The present invention therefore consists in optimizing an energy supply suitable for diarrheic calves, using products with high microbiological safety. The proportion of the energy in the form of carbohydrates, proteins and lipids, in the rehydrating mixture, is greatly modified with respect to the composition of milk.

The invention therefore relates to a rehydrating composition which can be used in particular for feeding young animals no longer able to digest milk, comprising:

lactose or glucose, or a lactose-based or glucose-based product, a mineral supplement ensuring restoration of the digestive losses, characterized in that the composition also comprises an effective amount of soluble plant proteins and of plant lipids which ensure suitable energy supply.

The carbohydrates can therefore be supplied in the form of glucose or lactose as has been described in previous patents concerning rehydration. The choice of lactose is most indicated, keeping a content substantially identical to that of milk (50 g lactose/l). It has been reported that intestinal lactase activity could be decreased in diarrheic calves, which is why lactose is often used in an amount lower than 50 g/l in various mixtures of rehydrating substances. The present invention recommends the use of a normal lactose content (preferably between 40 and 55 g/l) since the inventors have realized that lactase activity is increased by the presence of sodium, which makes it possible to transfer the hydrolysis products (glucose and galactose) to the enterocyte more rapidly. This increased transfer of the simple saccharides to the intestinal cell, in decreasing the concentration of the products of the lactase, facilitates its activity (which is located at the cell membrane on the intestinal lumen side). A large supply of carbohydrates is important not only for stimulating the intestinal absorption of sodium, but also for maintaining the glycemia, which is absolutely essential for the survival of the animal. Glucose, in particular 25 to 30 g/l, or lactose plus glucose: for example, 25 g of lactose and 13 g of glucose, may also be used as carbohydrate supply.

The present invention consists in replacing the soluble proteins of milk with proteins of plant origin. Isolates of plant proteins, in particular of soybean or gluten proteins, exist, however the latter are insoluble and, therefore, are not suitable for having an easily assimilable source of soluble proteins capable of directly crossing the gastric barrier. This difficulty is resolved by subjecting the isolates of plant proteins to suitable enzymatic treatment so as to have a mixture of peptides with a mean molecular weight of less than 20 000, in particular between 2 000 and 20 000. Besides their solubility, the advantage of using partially hydrolyzed plant proteins is to accelerate the rapidity of their intestinal digestion and to entirely inhibit their immunogenicity, which may be high when the intestinal mucous membrane is partially destroyed. Unlike the carbohydrates, the protein part in the composition of the rehydrating substance represents only 30% of the normal content of milk. In comparison with dairy proteins, soybean proteins are relatively low in sulfur-containing amino acids, while gluten is low in lysine.

The combination of the two types of protein (proteins low in sulfur-containing amino acids but rich in lysine and proteins low in lysine but rich in sulfur-containing amino acids) makes it possible to have an ideal composition of amino acids. In addition, the proteins are partially hydrolyzed, therefore their content and their nature are optimized for meeting the essential needs of the body while at the same time taking into account the metabolic problems linked in particular to the blocking of renal function in this hypovolemia situation (the animals stop urinating).

Preferably, the protein content is between 8 and 14 g/l.

In the same way as for proteins, the supply of lipids is essential. Preferably, the lipids are chosen from oils rich in medium-chain ($C_8$ to $C_{14}$) fatty acids and, optionally, soybean lecithin to solubilize said lipids. The use of solid copra or palm oil, the triglycerides of which are particularly rich in medium-chain fatty acids (with a chain length of 8 to 14 carbon atoms), facilitates their digestion since it is possible for these triglycerides to be hydrolyzed early by a gastric lipase. The solubilization of the lipids is ensured by a large supply of soybean lecithin, in particular in a proportion of 10% of the lipid supply. Reducing the lipid content with respect to milk and choosing easily digested fatty substances are essential since lipid digestion is greatly modified in diarrheic calves, which can, moreover, result in the appearance of severe steatorrhea. Preferably, the lipid content is between 8 and 12 g/l.

Preferably, the mineral supplement comprises cations chosen from the group consisting of sodium, potassium, magnesium and calcium cations in the form of mineral or organic salts.

Preferably, the mineral supplement comprises anions chosen from the group consisting of chloride, bicarbonate and phosphate ions, and acetate, propionate and citrate anions.

Also preferably, the cations or anions are supplied by mineral or organic salts chosen from the group consisting of sodium chloride, sodium bicarbonate, the salts of short-chain ($C_2$–$C_4$) fatty acids and of sodium, in particular sodium acetate or sodium propionate, potassium chloride, potassium hydrogen phosphate, magnesium chloride, calcium carbonate and citric acid.

Advantageously, the supplement will also comprise citric acid in order to destroy the bicarbonate and carbonate present.

The present invention therefore claims the use of 3 specific sources of energetic substrates for the preparation of a rehydrating mixture, in the following proportions:

lactose: 40 to 55 g/l partially hydrolyzed plant proteins: 8 to 14 g/l copra or palm triglycerides: 8 to 12 g/l, optionally combined with soybean lecithin from 0.6 to 1.2 g/l.

According to preferred variants, the proportions of the various mineral salts are indicated hereinafter:

The sodium supply must be considerable (between 70 and 90 mmol/l). This supply is intended to restore fecal sodium losses induced by the diarrhea, to facilitate the intestinal absorption of lactose and to reestablish the volemia (after the entry of water and sodium into the blood). In the present invention, the sodium is supplied in the form of bicarbonate, of chloride and of short-chain fatty acids (either acetate or propionate, or both acids) or of sodium citrate. Since the citric acid is in excess with respect to the bicarbonate, a portion of the sodium is therefore present in solution in the form of sodium citrate. The respective proportions of these three types of salt are as follows:

sodium chloride: 40 to 50% sodium bicarbonate: 0 to 50% sodium salts of short-chain fatty acids: 0 to 50%

In the present invention, the following proportion is recommended:

sodium chloride: 40%
  sodium bicarbonate: 48%
  salts of short-chain fatty acids in the form of sodium propionate: 12%.

Unlike sodium, potassium is an intracellular element, the losses of which are less significant than sodium in the event of diarrhea. However, they are far from negligible. In the present invention, it is recommended to supply 20 to 30 mM of potassium, maintaining the sodium/potassium ratio close to 3 with possible variations between 2.5 and 3.5. The potassium is preferably supplied in the form of potassium chloride and of potassium hydrogen phosphate:

potassium chloride: 60 to 80%
  potassium hydrogen phosphate: 20 to 40%

In the present invention, the following proportion is recommended:

potassium chloride: 70%
  potassium hydrogen phosphate: 30%.

With diarrhea, there is also a loss of various anions, in particular of chloride, of bicarbonate and of phosphate. The chloride replacement is ensured by supplying chlorides in the form of sodium, potassium and magnesium chlorides. The chloride concentration is preferably between 40 and 60 mM.

The possible distribution of the chloride salts is as follows:

sodium chloride: 50 to 70%
  potassium chloride: 25 to 50%
  magnesium chloride: 4 to 6%

In the present invention, the following proportion is recommended:

sodium chloride: 63%
  potassium chloride: 31.5%
  magnesium chloride: 5.5%.

It is also important not only to equilibrate the supply of the various chlorides, but also to have a sodium/chloride ratio greater than the ratio which exists in the blood (1.4). The optimum ratio is therefore between 1.5 and 1.6 and, in the present invention, it is 1.5.

With diarrhea, there is a very considerable loss of bicarbonate by the digestive tract; in addition, the poor irrigation of the tissues following the hypovolemia exacerbates the production of lactic acid, which creates a state of acidosis. Acidosis can be offset when the pH is maintained and only the bicarbonates are decreased, and/or can be much more severe when there is a drop in pH and depletion of bicarbonates. It is therefore necessary to provide bicarbonate and/or organic salts which generate bicarbonate after they have been metabolized, such as citric, acetic or propionic acids. Specifically, for example, when sodium acetate is supplied, the sodium is absorbed, and also the acetate, and the acetate is converted to CO2; since the organic anion has disappeared, it will be replaced with the bicarbonate, proportionally to the amounts of sodium absorbed. Certain rehydrating substances comprise bicarbonate, without supplying organic acids, which basifies the stomach. The raising of the gastric pH is very unfavorable for preserving the acidic microbial barrier normally present in this organ. In the present invention, bicarbonate is supplied, with citric acid, only with the aim of promoting effervescence in order to facilitate the dissolving of the energy-supplying mixture and of the mineral supplement. The supply of citric acid is sufficient to destroy all of the sodium bicarbonate and calcium carbonate; the pH of the solution is then close to 5.3; this makes it possible to have optimum appetence and to preserve the acidity of the gastric pH. When effervescence is not desired, there is perhaps no need to supply bicarbonate, and the excess of sodium with respect to the chloride will then be provided by the short-chain fatty acids (acetate, propionate) which will serve as delayed bicarbonate.

Diarrhea also brings about small losses of various electrolytes, in particular of phosphate, of calcium and of magnesium. In the present invention, phosphate is supplied in the form of potassium hydrogen phosphate, which makes it possible to stabilize the pH toward values close to 5; the recommended concentrations are from 5 to 10 mM.

Current synthetic rehydrating substances do not supply calcium, which greatly disturbs the calcium metabolism of animals undergoing very active growth. The objective of the rehydrating substance described, which is rich in assimilable energy and suitable for diarrheic calves, is also to maintain a basal calcium supply for bone tissue, but equally to serve as a buffer for intestinal fermentation, preferably a content between 7 and 12 mM. Theoretically, in the presence of phosphate, calcium is insoluble. In the present invention, the addition of citric acid for a pH close to 5 allows the solubilization of the calcium. For this reason, even though effervescence (bicarbonate, citric acid) is not essential, the rehydrating substance will, however, contain citric acid in order to solubilize the calcium which can be supplied simply in the form of carbonate. The citric acid/calcium molar ratio will be close to 1.5. The present invention also sets the molar ratios between calcium and phosphate in the range of 1 to 1.4, for a calcium supply ranging from 7 to 12 mM.

The mineral supplement also comprises small amounts of magnesium (1 to 3 mM) in the form of chloride, one of the most soluble salts of this element. In the present invention, the magnesium concentration is set at 1.5 mM.

Again preferably, the rehydrating composition comprises per liter, by weight:

| | |
|---|---|
| lactose | 40 to 55 g |
| hydrolyzed plant proteins, in particular hydrolyzed soybean and gluten proteins | 8 to 14 g |
| palm and/or copra oil | 8 to 12 g |
| soybean lecithin | 0.6 to 1.2 g | with the mineral supplement being supplied by one or more salts chosen from the group consisting of:

| | |
|---|---|
| sodium chloride | 2 to 4 g |
| sodium bicarbonate | 0 to 4 g |
| sodium propionate and/or acetate | 0 to 4 g |
| potassium chloride | 1 to 1.5 g |
| potassium hydrogen phosphate | 0.7 to 1.2 g |
| calcium carbonate | 0.5 to 1 g |
| magnesium chloride, 6H$_2$O | 0.1 to 0.6 g |
| citric acid | 1 to 5 g | and at a pH close to the stomach of the young animal (5 to 5.5).

Preferably, the energy supply of a composition according to the invention is between 30 and 70% [lacuna] of a composition similar to milk.

Preferably, the proportion of energy sources is as follows: 50 to 60% carbohydrates, 10 to 20% proteins, 25 to 35% lipids.

In the present invention, the following formulation is recommended:

lactose: 50 g/l, i.e. 200 kcal partially hydrolyzed soybean proteins: 6 g/l, i.e. 24 kcal partially hydrolyzed gluten proteins: 6 g/l, i.e. 24 kcal copra or palm triglycerides: 10 g/l combined with 1 g of soybean lecithin, i.e. 99 kcal, i.e. a total of 347 kcal with a carbohydrate proportion of 58%, a protein proportion of 14% and a lipid proportion of 28%, whereas a liter of milk containing 33% of fatty substance and of proteins supplies 629 kcal, including 32% for the carbohydrates, 21% for the proteins and 47% for the lipids.

This energy supply, which is very suitable for the physiopathological condition of sick or stressed young ruminants, is supplemented with a supply of minerals in order to restore the digestive losses.

By way of example, a typical composition of the rehydrating substance rich in assimilable energy was prepared:

| Energy-supplying portion: | |
|---|---|
| lactose | 50 g/l |
| hydrolyzed soybean proteins | 6 g |
| hydrolyzed gluten proteins | 6 g |
| solid palm or copra oil | 10 g |
| soybean lecithin | 1 g |
| Total weight | 73 g |
| Mineral supplement portion | |
| sodium chloride | 2.05 g (35 mM) |
| sodium bicarbonate | 3.57 g (42.5 mM) |
| sodium propionate | 0.96 g (10 mM) |
| potassium chloride | 1.3 g (17.5 mM) |
| potassium hydrogen phosphate | 1.02 g (7.5 mM) |
| calcium carbonate | 0.75 g (7.5 mM) |
| magnesium chloride, 6H$_2$O | 0.3 g (1.5 mM) |
| citric acid for destroying the bicarbonate and carbonate | 3.84 g (20 mM) |
| Total weight | 13.79 g |

The overall osmotic pressure is close to 360 mosmol, and the pH is 5.3.

The initial ionic composition of the mixture is as follows:

| | |
|---|---|
| sodium | 87.5 mM |
| potassium | 25 mM |
| magnesium | 1.5 mM |
| calcium | 7.5 mM |
| chloride | 55.5 mM |
| phosphate | 7.5 mM |
| bicarbonate | 42.5 mM |
| propionate | 10 mM |
| citric acid | 20 mM |

From the first symptoms of diarrhea, it is necessary to administer, if possible 3 times a day, 1 to 2 liters of the rehydrating mixture as described, this being until the animal is cured. If the calf has lost the sucking reflex, it is necessary to carry out rehydration via intravenous injection using a suitable rehydrating substance. This type of rehydrating substance makes it possible to cure more than 95% of calves and facilitates the recommencement of normal milk-based nutrition.

Of course, the invention is not limited to the embodiments described in the description. Those skilled in the art may envisage other variants without, however, straying from the context of the present invention. The incorporation into the composition of other saccharides, of amino acids and of small amounts of skimmed milk may in particular be envisaged, depending on the animal.

What is claimed is:

1. Energy-supplying rehydrating composition, which can be used in particular for feeding young animals no longer able to digest milk, comprising:

lactose or glucose, or a lactose-based or glucose-based product, a mineral supplement ensuring restoration of the digestive losses, an effective amount of soluble plant proteins and of plant lipids which ensure suitable energy supply, characterized in that the proportion of energy sources is as follows: 50 to 60% carbohydrates, 10 to 20% proteins, 25 to 35% lipids.

2. Rehydrating composition according to claim 1, characterized in that the mineral supplement comprises cations chosen from the group consisting of sodium, potassium, magnesium and calcium cations.

3. Rehydrating composition according to claim 1, characterized in that the mineral supplement comprises anions chosen from the group consisting of chloride, bicarbonate, phosphate, acetate, propionate and citrate anions.

4. Rehydrating composition according to either of claims 1 and 2, characterized in that the cations and anions are supplied by mineral or organic salts chosen from the group consisting of sodium chloride, sodium bicarbonate, the salts of short-chain (C$_2$–C$_4$) fatty acids and of sodium, in particular sodium acetate or sodium propionate, potassium chloride, potassium hydrogen phosphate, magnesium chloride, calcium carbonate and citric acid.

5. Rehydrating composition according to claim 2, characterized in that the cations and anions are supplied by mineral or organic salts chosen from the group consisting of sodium chloride, sodium bicarbonate, the salts of short-chain (C$_2$–C$_4$) fatty acids and of sodium, in particular sodium acetate or sodium propionate, potassium chloride, potassium hydrogen phosphate, magnesium chloride, calcium carbonate and citric acid.

6. Composition according to claim 5, characterized in that the soluble plant proteins are chosen from proteins low in sulfur-containing amino acids but rich in lysine, and proteins low in lysine but rich in sulfur-containing amino acids.

7. Composition according to claim 6, characterized in that it comprises hydrolyzed soybean proteins and hydrolyzed gluten.

8. Composition according to one of claims 1 and 5 to 7, characterized in that the lipids are chosen from oils rich in medium-chain (C8 to C14) fatty acids and, optionally, soybean lecithin in order to solubilize said lipids.

9. Composition according to claim 1, characterized in that the lipids are chosen from oils rich in medium-chain (C8 to C14) fatty acids and, optionally, soybean lecithin in order to solubilize said lipids.

10. Composition according to claim 1, characterized in that it comprises lactose.

11. Rehydrating composition according to one of the preceding claims, characterized in that the lactose content is between 40 and 55 g/l, in particular substantially identical to that of milk (approximately 50 g/l).

12. Rehydrating composition according to claim 1, characterized in that the lactose content is between 40 and 55 g/l, in particular substantially identical to that of milk (approximately 50 g/l).

13. Rehydrating composition according to claim 1, characterized in that the proportion of proteins is between 8 and 14 g/l.

14. Rehydrating composition according to claim 1, characterized in that the plant lipid content is between 8 and 12 g/l.

15. Rehydrating composition according to claim 1, characterized in that the sodium concentration is between 70 and 90 mM, the potassium concentration is between 20 and 30 mM and the sodium/potassium ratio is between 2.5 and 3.5.

16. Rehydrating composition according to claim 1, characterized in that the chloride anion content is between 40 and 60 mM and the sodium/chloride ratio is greater than 1.4, in particular between 1.5 and 1.6.

17. Rehydrating composition according to one of the preceding claims, characterized in that it comprises per liter, by weight:

| | |
|---|---|
| lactose | 40 to 55 g |
| hydrolyzed plant proteins, in particular hydrolyzed soybean and gluten proteins | 8 to 14 g |
| palm and/or copra oil | 8 to 12 g |
| soybean lecithin | 0.6 to 1.2 g | with the mineral supplement being supplied by one or more salts chosen from the group consisting of:

| | |
|---|---|
| sodium chloride | 2 to 4 g |
| sodium bicarbonate | 0 to 4 g |
| sodium propionate and/or acetate | 0 to 4 g |
| potassium chloride | 1 to 1.5 g |
| potassium hydrogen phosphate | 0.7 to 1.2 g |
| calcium carbonate | 0.5 to 1 g |
| magnesium chloride, 6H$_2$O | 0.1 to 0.6 g |
| citric acid | 1 to 5 g | and at a pH close to the stomach of the young animal.

18. Rehydrating composition according to claim 1, characterized in that it comprises per liter, by weight:

| | |
|---|---|
| lactose | 40 to 55 g |
| hydrolyzed plant proteins, in particular hydrolyzed soybean and gluten proteins | 8 to 14 g |
| palm and/or copra oil | 8 to 12 g |
| soybean lecithin | 0.6 to 1.2 g | with the mineral supplement being supplied by one or more salts chosen from the group consisting of:

| | |
|---|---|
| sodium chloride | 2 to 4 g |
| sodium bicarbonate | 0 to 4 g |
| sodium propionate and/or acetate | 0 to 4 g |
| potassium chloride | 1 to 1.5 g |
| potassium hydrogen phosphate | 0.7 to 1.2 g |
| calcium carbonate | 0.5 to 1 g |
| magnesium chloride, 6H$_2$O | 0.1 to 0.6 g |
| citric acid | 1 to 5 g | and at a pH close to the stomach of the young animal.

19. Rehydrating composition according to claim 1, characterized in that the energy supply of such a composition is between 30 and 70% of a composition similar to milk.

20. Rehydrating composition according to claim 1, for oral use.

* * * * *